(12) United States Patent
Salciccioli et al.

(10) Patent No.: US 10,017,433 B2
(45) Date of Patent: Jul. 10, 2018

(54) TRANSALKYLATED CYCLOHEXYLBENZYL AND BIPHENYL COMPOUNDS

(71) Applicant: ExxonMobil Chemical Patents Inc., Baytown, TX (US)

(72) Inventors: Michael Salciccioli, Houston, TX (US); Neeraj Sangar, League City, TX (US); Tan-Jen Chen, Kingwood, TX (US); Emiel de Smit, Brussels (BE); Ali A. Kheir, Sugar Land, TX (US); Aaron B. Pavlish, Humble, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/554,211

(22) PCT Filed: Dec. 16, 2015

(86) PCT No.: PCT/US2015/066109
§ 371 (c)(1),
(2) Date: Aug. 28, 2017

(87) PCT Pub. No.: WO2016/160084
PCT Pub. Date: Oct. 6, 2016

(65) Prior Publication Data
US 2018/0050971 A1    Feb. 22, 2018

Related U.S. Application Data

(60) Provisional application No. 62/140,723, filed on Mar. 31, 2015.

(30) Foreign Application Priority Data

Jun. 25, 2015 (EP) .................................... 15173771

(51) Int. Cl.
| | | |
|---|---|---|
| *C07C 6/12* | (2006.01) | |
| *C07C 5/11* | (2006.01) | |
| *C07C 5/367* | (2006.01) | |
| *C07C 2/74* | (2006.01) | |

(52) U.S. Cl.
CPC .............. *C07C 6/126* (2013.01); *C07C 2/74* (2013.01); *C07C 5/11* (2013.01); *C07C 5/367* (2013.01); *C07C 2521/04* (2013.01); *C07C 2529/08* (2013.01); *C07C 2529/12* (2013.01); *C07C 2601/14* (2017.05)

(58) Field of Classification Search
CPC ....... C07C 2/74; C07C 13/28; C07C 2529/74; C07C 2529/76; C07C 2601/14; C07C 2521/04; C07C 2529/08; C07C 2529/12; C07C 5/11; C07C 5/367; C07C 6/126; B01J 29/72; B01J 29/7276; B01J 29/7476; B01J 29/7676
See application file for complete search history.

(56) References Cited

U.S. PATENT DOCUMENTS

| | | |
|---|---|---|
| 6,037,513 A | 3/2000 | Chang et al. |
| 6,730,625 B1 | 5/2004 | Chang et al. |
| 9,328,053 B2 | 5/2016 | Bai et al. |
| 9,556,087 B2 | 1/2017 | Dakka et al. |
| 9,580,368 B2 | 2/2017 | Chen et al. |
| 9,580,572 B2 | 2/2017 | Dakka et al. |
| 9,688,602 B2 * | 6/2017 | Dakka ..................... C07C 67/08 |
| 9,708,230 B2 | 7/2017 | Salciccioli et al. |
| 9,725,377 B2 | 8/2017 | de Smit et al. |
| 9,758,447 B2 | 9/2017 | Dakka et al. |
| 9,856,186 B2 | 1/2018 | Salciccioli et al. |
| 9,896,393 B2 | 2/2018 | Salciccioli et al. |

(Continued)

FOREIGN PATENT DOCUMENTS

| | | |
|---|---|---|
| JP | 3603908 | 12/2004 |
| WO | 2010/138248 | 12/2010 |
| WO | 2012/082229 A | 6/2012 |

OTHER PUBLICATIONS

Bandyopadhyay et al., "Transalkylation of Cumene with Toluene over Zeolite-Beta," Applied Catalysis A: General, 1996, vol. 135, pp. 249-259.

Bandyopadhyay et al., "Transalkylation Reaction—An Alternative Route to Produce Industrially Important Intermediates Such as Cymene," Catalysis Today, 1998, vol. 44, pp. 245-252.

Mavrodinova et al., "Transalkylation of toluene with cumene over zeolites Y dealuminated in solid-state, Part I: Effect of the alteration of Broensted acidity," Applied Catalysis A: General, 2003, vol. 248, pp. 181-196.

Mavrodinova et al., "Transalkylation of Toluene with Cumene over Zeolites Y Dealuminated in Solid-state Part II. Effect of the introduced Lewis Acid Sites," Applied Catalysis A: General, 2003, 248, pp. 197-209.

(Continued)

*Primary Examiner* — Sharon Pregler

(57) ABSTRACT

Processes for selectively alkylating and/or dealkylating one ring of cyclohexylbenzyl and/or biphenyl compounds are provided. Such selective alkylation and/or dealkylation takes place through a transalkylation reaction between the cyclohexylbenzyl compound and a substituted or unsubstituted benzene, which replaces the phenyl moiety of the cyclohexylbenzyl compound. The transalkylated cyclohexylbenzyl may be dehydrogenated to give a corresponding biphenyl compound. The same reaction steps can be utilized with respect to biphenyl compounds by first partially hydrogenating one phenyl ring of the biphenyl compound, thereby obtaining a corresponding cyclohexylbenzyl compound, which may undergo the transalkylation and, optionally, subsequent dehydrogenation. Combinations of any two or more of partial hydrogenation, transalkylation, and dehydrogenation enable targeted substitution (or de-substitution) of only one ring of cyclohexylbenzyl and/or biphenyl compounds, thereby providing superior control in designing the synthesis of these compounds.

23 Claims, 1 Drawing Sheet

(56) References Cited

U.S. PATENT DOCUMENTS

2014/0275609 A1  9/2014  Dakka et al.
2018/0030219 A1  2/2018  Chung et al.

OTHER PUBLICATIONS

Borodina et al., "Hydroalkylation of Benzene and Ethylbenzene over Metal-Containing Zeolite Catalysts," Chemistry, 2009, vol. 49 pp. 66-72.
Lu et al., "Selective Hydrogenation of Single Benzene Ring in Biphenyl Catalyzed by Skeletal Ni," ChemCatChem, 2009, vol. 1:3, pp. 369-371.

* cited by examiner

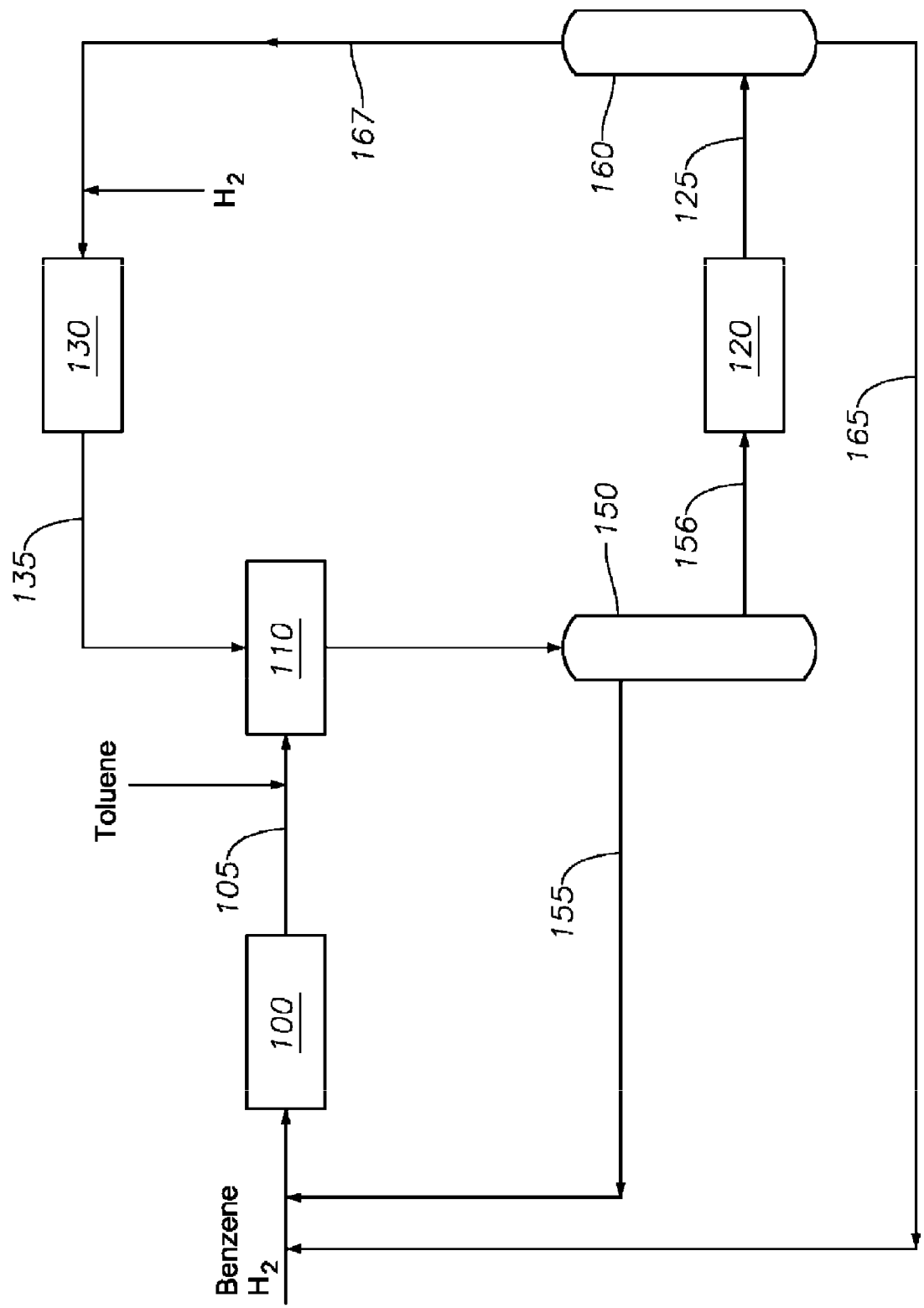

TRANSALKYLATED CYCLOHEXYLBENZYL AND BIPHENYL COMPOUNDS

PRIORITY

This application is a National Phase Application claiming priority to and the benefit of PCT Application Serial No. PCT/US2015/066109, filed Dec. 16, 2015, and U.S. Ser. No. 62/140,723, filed Mar. 31, 2015, the disclosures of which are incorporated herein by reference in their entirety.

FIELD OF THE INVENTION

This disclosure relates to a process for the preparation of cyclohexylbenzyl compounds and/or biphenyl compounds alkylated at targeted positions on said compounds.

RELATED APPLICATIONS

This application is related to U.S. Provisional Patent Application No. 62/012,024.

BACKGROUND OF THE INVENTION

Cyclohexylbenzyl compounds such as cyclohexylbenzene are useful intermediates in the production of a variety of other commercially valuable intermediates and precursors, such as biphenyl compounds (which, themselves, are useful intermediates in production of polyesters, plasticizers, and other polymer compositions, among other things) and phenol and/or cyclohexanone (which itself is a useful intermediate in, e.g., caprolactam for nylon production).

One of the most convenient means to produce cyclohexylbenzyls such as cyclohexylbenzene is hydroalkylation of co-fed benzene and hydrogen using a hydroalkylation catalyst, such as described in U.S. Pat. No. 6,037,513. Substituted cyclohexylbenzyl compounds, such as alkyl-substituted cyclohexylbenzyl compounds, may be formed by utilizing toluene, xylene, or another alkylbenzene in place of benzene in the hydroalkylation process.

Unfortunately, hydroalkylation offers little in the way of control of alkylation position. For instance, in the hydroalkylation of toluene to obtain methylcylohexyltoluene (MCHT), the reaction product will contain alkyl substitutions on both the cyclohexyl and the phenyl rings of the compound. While a hydroalkylation feed comprising both toluene and benzene could result in some cyclohexylbenzyl species having a methyl substitution on only one of the two rings, control as to which of the two rings have that substitution is still difficult, and furthermore, the reaction products would contain significant amounts of unsubstituted cyclohexylbenzene and the di-substituted MCHT species.

Furthermore, even among the MCHT species, it is difficult to control the positions of the alkyl substitutions on each ring. For instance, MCHT can be dehydrogenated to provide dimethylbiphenyl (DMBP). DMBP can readily be converted to an ester plasticizer by a process comprising oxidation of the DMBP to produce the corresponding mono- or dicarboxylic acid followed by esterification with a long chain alcohol. However, for certain uses, only particular positional isomers of DMBP are useful. For instance, 2,X' DMBP (where X' is 2', 3', or 4') isomers are not preferred in a final product since, for example, diphenate esters having substitution on the 2-carbons tend to be too volatile for use as plasticizers. Even using a selective molecular sieve catalyst for the hydroalkylation step, the process tends to yield a mixture of all six DMBP positional isomers (2,2', 2,3', 2,4', 3,3', 3,4', and 4,4' DMBP), including up to about 20% by weight or more of the undesired 2,X' DMBP isomers, which cannot easily be separated from unreacted MCHT by distillation due to an overlap in their vapor-liquid equilibrium properties.

There is therefore a need for a means of producing selectively alkylated cyclohexylbenzyl and biphenyl compounds, offering some control over the position(s) of alkyl substitutions in such compounds.

Additional references of interest may include U.S. Pat. No. 6,730,625; U.S. Patent Publication nos. 2014/0275605, 2014/0275606, 2014/0275607, 2014/0275609, 2014/0323782; and WIPO Publication No. WO 2010138248 A2. Further references include Bandyopadhyay et al., "Transalkylation of Cumene with Toluene over Zeolite-Beta," *Applied Catalysis A: General*, 135 (1996) 249; Bandyopadhyay et al., "Transalkylation Reaction—An Alternative Route to Produce Industrially Important Intermediates Such as Cymene," *Catalysis Today*, 44 (1998) 245; Mavrodinova et al., "Transalkylation of toluene with cumene over zeolites Y dealuminated in solid-state, Part I: Effect of the alteration of Broensted acidity," *Applied Catalysis A: General*, 248 (2003) 181; Mavrodinova et al., *Applied Catalysis A: General*, 248 (2003) 197; Borodina et al., *Petroleum Chemistry*, 49 (2009) 66; and Lu et al., "Selective Hydrogenation of Single Benzene Ring in Biphenyl Catalyzed by Skeletal Ni," *ChemCatChem*, 1:3 (2009) 369.

SUMMARY OF THE INVENTION

The present invention provides for selectively alkylated cyclohexylbenzyl and/or biphenyl compounds, and methods to obtain them. In particular, processes according to the present invention employ transalkylation of a cyclohexylbenzyl compound, in some embodiments in combination with other processing steps such as dehydrogenation and/or hydrogenation, to obtain cyclohexylbenzyl compounds and/or biphenyl compounds with alkyl substitutions at controlled locations on those compounds.

Processes according to the invention therefore include transalkylating a substituted or unsubstituted cyclohexylbenzyl compound with a substituted or unsubstituted benzene in the presence of a transalkylation catalyst, thereby obtaining a substituted or unsubstituted cyclohexylbenzene transalkylation product. For instance, cyclohexylbenzene may be transalkylated with an alkylbenzene (e.g., toluene, ethylbenzene, etc.) according to the following reaction, wherein R represents a $C_1$-$C_{10}$ alkyl group:

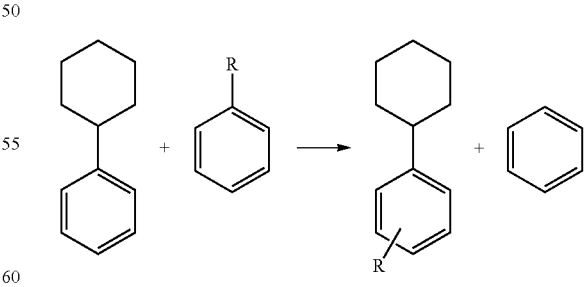

As can be seen, the transalkylation reaction effectively provides for targeted addition of alkyl groups on only the phenyl ring of a cyclohexylbenzyl compound. The reaction in some embodiments may be carried out with a cyclohexylbenzyl group having any of 1, 2, 3, 4, and 5 substitutions (preferably $C_1$-$C_{10}$ alkyl substitutions) on either or both of the cyclohexyl ring or the phenyl ring of such compound, as illustrated by formula (I) of the reaction shown below, wherein each $R^1$-$R^{10}$ is independently H or $C_1$-$C_{10}$ alkyl. Furthermore, as also shown in the reaction scheme below, the alkylbenzene with which the cyclohexylbenzyl compound is transalkylated may in general be a substituted or unsubstituted benzene according to Formula (II), wherein $R^{6*}$-$R^{10*}$ are each independently H or $C_1$-$C_{10}$ alkyl. The reaction forms a transalkylated cyclohexylbenzyl compound according to the formula (III) (and/or positional isomers thereof), where each $R''$ and $R''^*$ is as previously defined.

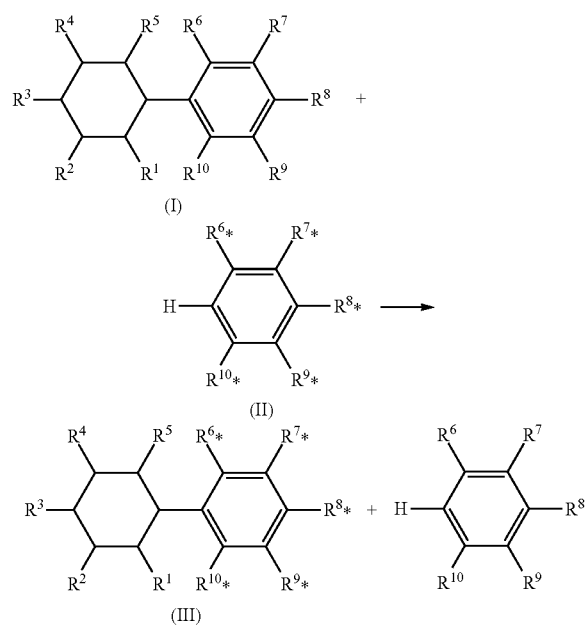

In some embodiments, the cyclohexylbenzyl compound may be obtained by partially hydrogenating a biphenyl compound of formula (IV), shown below (where each $R^1$-$R^{10}$ is as previously defined for formula (I)). Further, the transalkylated cyclohexylbenzyl compound of formula (III) may, in some embodiments, be dehydrogenated to give a corresponding ring-replaced biphenyl compound of formula (V), also shown below (where each $R''$ and $R''^*$ is as previously defined for formula (III)):

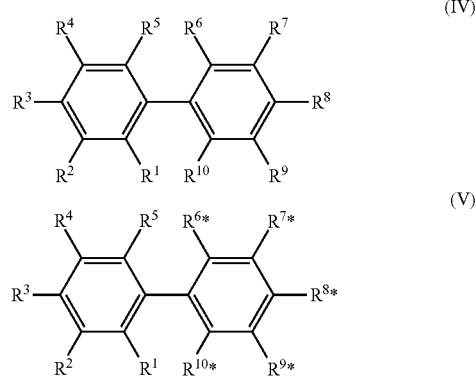

The overall process of some embodiments may, therefore, include (i) partially hydrogenating a precursor biphenyl compound to a corresponding cyclohexylbenzyl compound; (ii) transalkylating the cyclohexylbenzyl compound with an alkylbenzene so as to obtain a transalkylated cyclohexylbenzyl compound; and (iii) dehydrogenating the transalkylated cyclohexylbenzyl compound to obtain a ring-replaced biphenyl compound, wherein one phenyl ring of the ring-replaced biphenyl compound comprises different substitutions than the corresponding ring of the precursor biphenyl compound. The end result according to such embodiments, in other words, is a targeted alkylation of only one ring of a biphenyl compound. This allows for advantageously targeted molecular design of biphenyl compounds (e.g., production of alkylbiphenyl compounds with alkyl substitution(s) on only one ring of the biphenyl compound), and/or could find application in isomerization reactions (e.g., replacing undesirable substitutions on one ring of a biphenyl compound with desirable substitutions, and/or removing undesirable substitutions entirely by transalkylating with unsubstituted benzene).

According to yet further embodiments, the process may be repeated using the second biphenyl compound as a starting point, so as to selectively alkylate the other ring of the biphenyl compound (e.g., the ring that did not undergo transalkylation in the prior reaction steps). Processes according to such embodiments therefore further include (iv) partially hydrogenating the ring-replaced biphenyl compound so as to obtain a semi-substituted cyclohexylbenzyl compound (e.g., partially hydrogenating the alkylated ring of the alkylbiphenyl); (v) transalkylating the ring-replaced cyclohexylbenzyl compound with a second alkylbenzene (which may be the same as or different from the first alkylbenzene of step (ii)) to as to obtain a further transalkylated cyclohexylbenzyl compound; which is then (vi) dehydrogenated to obtain the corresponding double ring-replaced biphenyl compound, wherein both rings of the double ring-replaced biphenyl compound have different substitutions than the rings of the first biphenyl compound.

In yet other embodiments, rather than using an alkylbenzene in either or both of steps (ii) and (v) above, an unsubstituted benzene may be used, which would result in effectively removing any unwanted substitutions from the phenyl ring of the cyclohexylbenzyl compound being transalkylated with the benzene. Combined with the surrounding partial hydrogenation and dehydrogenation steps, in this way, unwanted substitutions on either or both rings of a biphenyl compound could be removed.

Yet further embodiments may include a combination hydroalkylation and transalkylation reaction, utilizing either a bifunctional catalyst (which catalyzes hydroalkylation and transalkylation reactions) or multiple catalysts (each catalyst performing a separate function), such as a hydrogenation catalyst and an alkylation catalyst. The feed to such a combined reaction may comprise hydrogen, a substituted or unsubstituted benzene, and either or both of a cyclohexylbenzyl compound and a biphenyl compound. A combination of hydrogenation, hydroalkylation, and transalkylation may take place in the presence of the bifunctional catalyst (or multiple catalysts), so as to co-produce both a transalkylation product and a hydroalkylation product. A bifunctional catalyst according to some embodiments comprises a hydrogenation component and a molecular sieve. Similarly, multiple catalysts according to some embodiments include a hydrogenation catalyst (e.g., a hydrogenation component) and an alkylation catalyst (e.g., a molecular sieve). Utilizing molecular sieves of different silica and alumina compositions (either in a bifunctional catalyst or as an alkylation catalyst) may, in some embodiments, increase selectivity to the transalkylation products at the expense of hydroalkylation products, and vice-versa. Performing such combined reactions, in many cases, will lead to a reduction in net process costs by eliminating the need for additional reactor vessels. Additionally, the increase in higher molecular-weight liquid feed (e.g., either or both of the cyclohexylbenzyl and biphenyl compounds) to the reactor can act as sensible heat to reduce the severity of the exotherm associated with hydroalkylation.

BRIEF DESCRIPTION OF THE DRAWINGS

FIG. 1 is a simplified process flow diagram illustrating a transalkylation and hydroalkylation process in accordance with some embodiments of the invention.

DETAILED DESCRIPTION OF THE EMBODIMENTS

Processes for the advantageous targeted alkylation of cyclohexylbenzyl and/or biphenyl compounds are provided herein. The processes each take advantage of the ability to selectively transalkylate a cyclohexylbenzyl compound so as to replace the phenyl ring of said cyclohexylbenzyl compound with another phenyl ring having desired substitutions (or, if preferred, a phenyl ring having no substitutions). This transalkylation may be utilized in combination with various surrounding reactions, such as dehydrogenation and partial hydrogenation, to provide for targeted alkylation of, and/or replacement of substitutions on, a single ring of a two-ring compound such as a cyclohexylbenzyl compound and/or a biphenyl compound.

Definitions

As used herein, a "substituted" hydrocarbon is one in which at least one H on the hydrocarbon has been replaced with another moiety, such as an alkyl, alkenyl, alkynyl, aryl, or other functional group. Similarly, a "substitution" is the moiety that has replaced an H on the hydrocarbon. By way of illustration, a "substituted" benzene is one in which at least one H has been replaced by another moiety, and that other moiety is the "substitution" on that benzene. For instance, an alkyl-substituted benzene is a benzene in which at least one H has been replaced by an alkyl group (e.g., toluene, wherein a methyl group is the substitution).

By contrast, an "unsubstituted" hydrocarbon is one in which none of the Hs have been substituted with another moiety. For instance, an unsubstituted benzene is a benzene molecule with no pendant moieties. Likewise, an unsubstituted cyclohexylbenzene is a cyclohexylbenzene with no additional moieties.

A "cyclohexylbenzyl" or a "cyclohexylaromatic" compound, as used herein, is a benzene molecule substituted at one position with a cyclohexane moiety, which moiety itself may or may not be further alkyl substituted. Further, the benzene of the cyclohexylbenzyl compound may or may not have additional substitutions. Thus, examples of cyclohexylbenzyl compounds include cyclohexylbenzene (wherein neither the cyclohexane moiety nor the benzene moiety contain further substitutions); methylcyclohexylbenzene (wherein the cylcohexane moiety contains a methyl substitution); methylcyclohexyltoluene (wherein each of the cylcohexane and the benzene moieties additionally contains a methyl substitution); ethylcyclohexyltoluene (wherein the cyclohexane moiety contains an ethyl substitution and the benzene moiety contains a methyl substitution); and so on.

A "ring-replaced" compound is a shorthand term that refers to a cyclohexylbenzyl or biphenyl compound in which one of the two hydrocarbon rings (in the case of cyclohexylbenzyl, the hexyl or phenyl ring; in the case of biphenyl, one of the two phenyl rings) has been replaced by another ring having different substitutions, via a process including a transalkylation reaction. A "double ring-replaced" compound, similarly, refers to a cyclohexylbenzyl or biphenyl compound in which both hydrocarbon rings have been so replaced.

Along a similar vein, a "transalkylated cyclohexylbenzyl compound" refers to a cyclohexylbenzyl compound that has had its phenyl ring replaced via a transalkylation reaction, and a "further transalkylated cyclohexylbenzyl compound" refers to a cyclohexylbenzyl compound that has undergone a further transalkylation, wherein the cyclohexylbenzyl compound prior to the further alkylation underwent a first transalkylation followed by dehydrogenation, and partial rehydrogenation such that the replaced ring from the first transalkylation is the saturated (hexyl) moiety.

A "(alkylcyclohexyl)benzene" compound or an "(alkylcyclohexyl)aromatic" compound is a cyclohexylbenzyl compound wherein the cyclohexane moiety is further substituted by one or more $C_1$-$C_{10}$ aliphatic alkyl groups. Similarly, where the benzene moiety of a cyclohexylbenzyl compound is further substituted with one or more $C_1$-$C_{10}$ aliphatic alkyl groups, the cyclohexylbenzyl compound may more specifically be referred to as a "cyclohexyl(alkylbenzene)" or a "cyclohexyl(alkylaromatic)" compound. Likewise, an "(alkylcyclohexyl)alkylbenzene" is a cyclohexylbenzyl compound having one or more substitutions (which may be the same or different) on each of its cylcohexyl and phenyl rings. Such a cyclohexylbenzyl compound may also be referred to as a "polyalkylated" cyclohexylbenzene (e.g., a cyclohexylbenzyl compound having more than one alkyl substitution).

An "alkylbiphenyl" compound is a biphenyl with at least one $C_1$-$C_{10}$ aliphatic alkyl substitution. A "polyalkylbiphenyl" compound has more than one such substitutions.

As used herein, a "$C_x$ hydrocarbon", where x is an integer, refers to a hydrocarbon compound having X carbon atoms. Thus, a $C_6$ hydrocarbon is a hydrocarbon having 6 carbon atoms. A "$C_x$-$C_y$ hydrocarbon" is a hydrocarbon having from x to y carbon atoms (e.g., a $C_6$-$C_{10}$ hydrocarbon is a hydrocarbon having 6, 7, 8, 9, or 10 carbon atoms); a "$C_x$ or greater" hydrocarbon is a hydrocarbon having x or more carbon atoms; and a "greater than $C_x$ hydrocarbon" is a hydrocarbon having more than x carbon atoms. Similarly, a "$C_x$ or less" hydrocarbon is one having x or fewer carbon atoms, and "a less than $C_x$" hydrocarbon is one having fewer than x carbon atoms.

A "positional isomer" or "regioisomer," as used herein, refers to a compound in which a functional group or other moiety changes position on a parent structure. Such terms are used herein in conjunction with depictions of structural formulas. Thus, in other words, a "positional isomer" or "regioisomer" of a compound having one or more R-groups is defined as a compound having the same parent structure depicted in the structural formula, but with the R-group(s) in a different position. For instance, a compound having multiple R-groups may have a regioisomer in which two or more of the R-groups have switched place with one another. Examples of Regioisomers may be seen in the following formulas (I) and (I-i), with (I-i) being a positional isomer, or regioisomer, of (I):

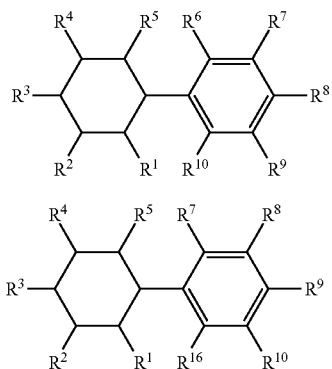

As can be seen, the $R^6$-$R^{10}$ groups of the right-side ring in formula (I) are rotated counterclockwise one position around the right-side phenyl ring in formula (I-i). Otherwise, the parent structure (here, a cyclohexylbenzene with R groups $R^1$-$R^{10}$ appended thereto) remains the same. Thus, (I) and (I-i) are positional isomers, or regioisomers. This is in contrast with the pair cyclohexylbenzene and hex-1-enyl benzene, which, despite both having the chemical formula $C_{12}H_{16}$, are not positional isomers of each other due to the different carbon chains about which the R-groups are positioned (cyclohexylbenzene, a two-ring compound, versus hexenylbenzene, a benzene having an alkenyl substitution (hex-1-enyl)).

Transalkylation of Cyclohexylbenzyl Compounds

In its most general form, the transalkylation reaction of embodiments of the present invention is represented by the reaction shown below, which depicts transalkylation of a cyclohexylbenzyl compound of formula (I) with a substituted or unsubstituted benzene of formula (II). The reaction is carried out in the presence of a transalkylation catalyst and under transalkylation conditions suitable to produce a transalkylation reaction product comprising a cyclohexylbenzyl compound of formula (III) (and positional isomers thereof).

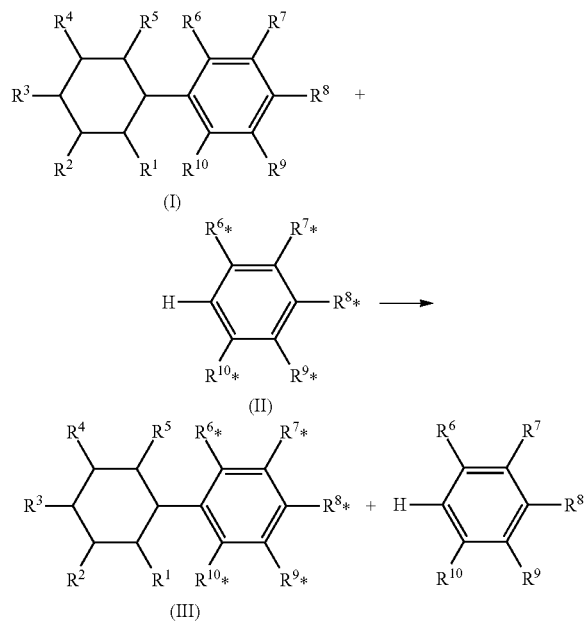

In formula (I), each of $R^1$, $R^2$, $R^3$, $R^4$, $R^5$, $R^6$, $R^7$, $R^8$, $R^9$, and $R^{10}$ is independently selected from the group consisting of H and $C_1$-$C_{10}$ alkyl groups, preferably non-aliphatic alkyl groups. Similarly, in formula (II), each of $R^{6*}$, $R^{7*}$, $R^{8*}$, $R^{9*}$, and $R^{10*}$ is likewise independently selected from the group consisting of H and $C_1$-$C_{10}$ alkyl groups, preferably non-aliphatic alkyl groups, provided that one or more of the following is true: $R^{6*}$ is different from $R^6$, $R^{7*}$ is different from $R^7$, $R^{8*}$ is different from $R^8$, $R^{9*}$ is different from $R^9$, and $R^{10*}$ is different from $R^{10}$.

In certain preferred embodiments, one or two of $R^{6*}$-$R^{10*}$ is methyl ($C_1$ alkyl), and the rest of $R^{6*}$-$R^{10*}$ are each H. Thus, in such embodiments, the substituted or unsubstituted benzene of formula (II) is toluene and/or xylene. In certain other embodiments, one of $R^{6*}$-$R^{10*}$ is ethyl, and the rest of $R^{6*}$-$R^{10*}$ are each H (i.e., the substituted or unsubstituted benzene of formula (II) is ethylbenzene). In yet other embodiments, each of $R^{6*}$, $R^{7*}$, $R^{8*}$, $R^{9*}$, and $R^{10*}$ is H (i.e., the compound according to formula (II) is benzene). In further embodiments, $R^1$-$R^5$ are each methyl or H, and in such embodiments, preferably only two or less (i.e., 0, 1, or 2) of $R^1$-$R^5$ are methyl.

As can be seen, the reaction essentially involves the targeted replacement of (a) the benzene moiety of the cyclohexylbenzyl compound of formula (I) with (b) the substituted or unsubstituted benzene of formula (II). In this way, one can obtain a cyclohexylbenzene having one or more alkyl substitutions specifically located on the phenyl ring of the cyclohexylbenzene, by selecting a substituted benzene with desired pendant R-groups ($R^{6*}$-$R^{10*}$). Or, similarly, one can effectively (i) remove or (ii) replace unwanted benzene-ring substitutions within a cyclohexylbenzene compound by, respectively: (i) transalkylating the cyclohexylbenzene with an unsubstituted benzene; or (ii) transalkylating the cyclohexylbenzene with a benzene having the desired R-group(s) substituted thereon.

For instance, a cyclohexylbenzene could be transalkylated to a (cylcohexyl)toluene with reliable location of the methyl group on the phenyl ring, according to the following reaction (where R is methyl):

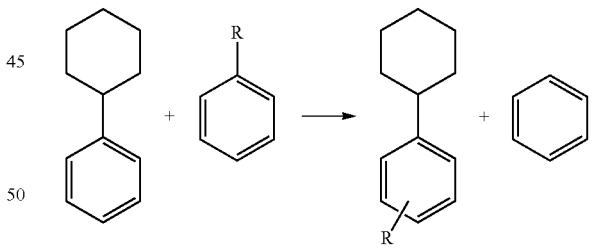

As another example, a (methylcyclohexyl)ethylbenzene could be transalkylated to a (methylcyclohexyl)toluene, or to a (methylcyclohexyl)benzene. According to yet further examples, cyclohexylbenzene could be transalkylated with xylene to give cyclohexylxylene (which could, in turn, be dehydrogenated as discussed in more detail below, thereby giving a dimethylbiphenyl compound in which both methyl groups are on a single phenyl ring).

Yet further examples include isomerization reactions, such as transalkylation of (methylcyclohexyl)toluenes having the methylcyclohexyl substitution at the 2-position on the toluene (e.g., 2,x-(methylcyclohexyl)toluene, where x may be 3, or 4). As described in WIPO Patent Publication WO/2014159100 A1, at Paragraph [0027], (methylcyclohexyl)toluenes having a methyl group in the 2 position on either the cyclohexyl or phenyl ring (including 2,x-(methylcyclohexyl)toluenes) are precursors for the formation of fluorene and methylfluorene in a synthesis process for producing biphenyl plasticizers from toluene hydroalkylation (in which methylcyclohexyltoluene is an intermediate). Fluorene is difficult to separate from the dimethylbiphenyl product of such processes, and may further cause problems in later steps (e.g., oxidation) of those processes. As such, transalkylation of the (methylcyclohexyl)toluenes having methyl groups in the 2-position on the phenyl ring (e.g., with additional toluene) will help reduce the presence of these undesired isomers, at least because any reaction product using the undesired isomer as feed will have a mixture of desired and undesired isomers. But moreover, it is believed that due to steric issues, the transalkylation reaction with further toluene will favor (methylcyclohexyl)toluene isomers that do not have methyl groups in the 2-position on the phenyl ring. Furthermore, processes according to various embodiments may also help reduce the presence of isomers having methyl groups in the 2 position on the cyclohexyl ring, when transalkylation is combined with dehydrogenation and partial hydrogenation, as described in more detail below.

According to yet further embodiments, in any process where only certain isomers of a substituted cyclohexylbenzyl molecule are desired, transalkylation as described herein can be used to increase the carbon efficiency of the process by converting undesired isomers to desired isomers.

The transalkylation reaction can be conducted over a wide range of conditions but in most embodiments is effected at a temperature from about 75° C. to about 250° C., such as from about 100° C. to about 200° C., for example about 125° C. to about 160° C.; and a pressure from about 100 to about 3550 kPa-absolute, such as from about 1000 to about 1500 kPa-absolute.

The transalkylation catalyst may be a solid acid catalyst, such as a molecular sieve and in particular a molecular sieve having a large pore molecular sieve having a Constraint Index (as defined in U.S. Pat. No. 4,016,218) less than 2. Suitable large pore molecular sieves include zeolite beta, zeolite Y, Ultrastable Y (USY), Dealuminated Y (Deal Y), mordenite, ZSM-3, ZSM-4, ZSM-18, ZSM-20, and mixtures thereof, with zeolite beta and zeolite Y being preferred in some embodiments. Other suitable molecular sieves include molecular sieves of the MCM-22 family, including MCM-22 (described in U.S. Pat. No. 4,954,325), PSH-3 (described in U.S. Pat. No. 4,439,409), SSZ-25 (described in U.S. Pat. No. 4,954,325), PSH-3 (described in U.S. Pat. No. 4,439,409), SSZ-25 (described in U.S. Pat. No. 4,826,667), ERB-1 (described in EP 0 293 032), ITQ-1 (described in U.S. Pat. No. 6,077,498), ITQ-2 (described in WO 97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof.

Partial Hydrogenation of Biphenyl Compounds to Cyclohexylbenzyl Compounds

The above-described process can also suitably be used in processes according to some embodiments, in which one phenyl ring of a biphenyl compound is selectively alkylated and/or dealkylated. In particular, desired substitutions can be added to just one phenyl ring of a biphenyl compound, and undesired substitutions on one phenyl ring of a biphenyl can be removed and/or replaced, according to various embodiments.

Therefore, processes according to such embodiments include partially hydrogenating a biphenyl compound according to formula (IV) (shown below) so as to obtain a partial hydrogenation reaction effluent comprising a cyclohexylbenzyl compound according to formula (I) above (and, optionally, positional isomers thereof), as shown in the partial hydrogenation reaction depicted below. The cyclohexylbenzyl compound according to formula (I) can, as already described, then be subjected to a targeted transalkylation reaction.

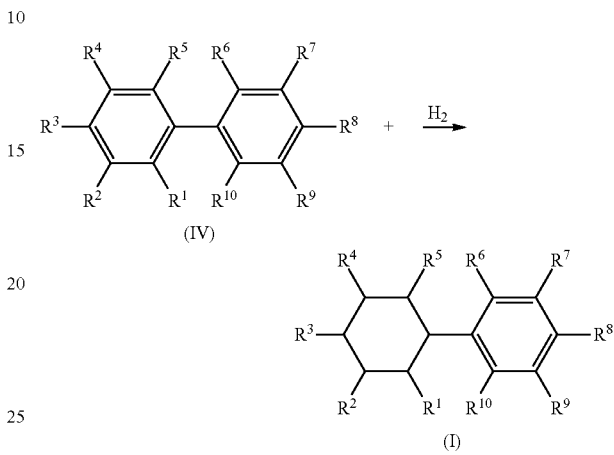

In formula (IV), each $R^1$-$R^{10}$ is defined in the same manner as the $R^1$-$R^{10}$ of formula (I), already defined previously.

The target product of the partial hydrogenation of a biphenyl compound according to formula (IV) is the cyclohexylbenzyl compound of formula (I) and positional isomers thereof in which $R^6$-$R^{10}$ are located on the phenyl ring of formula (I). In other words, the partial hydrogenation reaction preferably should result in hydrogenation of only one of the two phenyl rings is hydrogenated. Furthermore, it will be appreciated that where only one phenyl ring contains undesired substitutions (e.g., where one or more of $R^6$-$R^{10}$ is an undesired substitution), the target product of the partial hydrogenation is the cyclohexylbenzyl compound in which $R^6$-$R^{10}$ are located on the phenyl ring of the cyclohexylbenzyl compound.

The selectivity of hydrogenation toward the partially saturated product can be increased through limiting the overall conversion, optimization of operating conditions, or design and use of effective catalysts. For instance, by choosing a particular hydrogenation component (e.g., palladium, or in some cases, a S—Ni (skeletal Ni) catalyst), concentration of the hydrogenation component, zeolite function, and zeolite concentration (vs. metal concentration and binder concentration), selectivity to the partially hydrogenated product may be tuned. Other options include lowering hydrogen partial pressure, or modifying reaction conditions to similar effect.

At any rate, any hydrogenation reaction of a biphenyl compound should yield at least some partially hydrogenated species, which may be separated out from other products; increasing selectivity to such species of course increases efficiency, but any hydrogenation may be used in combination with separation to obtain the partially hydrogenated product. For instance, in some cases, the target cyclohexylbenzyl partial hydrogenation product may be co-produced with bicyclohexyl compounds (e.g., as a result of complete hydrogenation), and/or with cyclohexylbenzyl compounds in which the cyclohexyl ring, not the phenyl ring, contains the undesired substitutions (continuing the example of desired partial hydrogenation from above, such cyclohexylbenzyl compounds represent the case where one or more of the $R^6$-$R^{10}$ is an undesired substitution, but the $R^6$-$R^{10}$ are located on the cyclohexyl ring, while the $R^1$-$R^{10}$ are located on the phenyl ring). It will be readily apparent to the ordinarily skilled artisan that, for the transalkylation reactions described herein to serve the purpose of replacing or removing undesired substitutions, such undesired substitutions must be present on the phenyl ring, not the cyclohexyl ring.

That is, obtaining the partial hydrogenation product may further comprise separating the target partial hydrogenation product (e.g., the cyclohexylbenzyl positional isomers according to formula (I) wherein $R^6$-$R^{10}$ are located on the phenyl ring) from other cyclohexylbenzyl compounds (e.g., other positional isomers) and/or bicyclohexyl compounds in the hydrogenation reaction effluent. Such separation can conveniently be carried out by, e.g., fractionation, distillation, and the like, where the target positional isomers have different boiling points from the byproduct positional isomers. Instead or in addition, separations such as crystallization, adsorption, absorption, and/or liquid-liquid extraction may be used to obtain the target cyclohexylbenzyl partial hydrogenation product.

Furthermore, any undesired species (e.g., fully hydrogenated bicyclohexyl compounds, or cyclohexylbenzyl compounds in which the wrong ring is hydrogenated) may, after separation (either immediately after, or further downstream in an integrated process), be recycled to the partial hydrogenation reaction in order to increase system efficiency. The partial hydrogenation reaction can take place in the presence of a hydrogenation catalyst, under conditions suitable to provide the target partial hydrogenation product. Suitable hydrogenation catalysts include a hydrogenation metal. Any known hydrogenation metal or compound thereof can be employed, although suitable metals in particular include those selected from group 10 of the Periodic Table of the Elements (in particular palladium and nickel, such as skeletal nickel and/or raney nickel), and/or copper, ruthenium, nickel, zinc, and cobalt. The hydrogenation catalyst is preferably a supported hydrogenation metal catalyst, with the support having a small (narrow) particle size distribution. Example supports include $SiO_2$, $Al_2O_3$, carbon, and any combination thereof.

Dehydrogenation of Cyclohexylbenzyl Compounds to Biphenyl Compounds

The cyclohexylbenzyl compounds obtained by the transalkylation reaction described above (e.g., compounds according to formula (IV)) may in turn be dehydrogenated to provide a corresponding biphenyl compound. Processes of some embodiments therefore further include dehydrogenating a transalkylated cyclohexylbenzyl compound (e.g., according to formula (III)) to a corresponding biphenyl compound (e.g., according to formula (V)), as shown below.

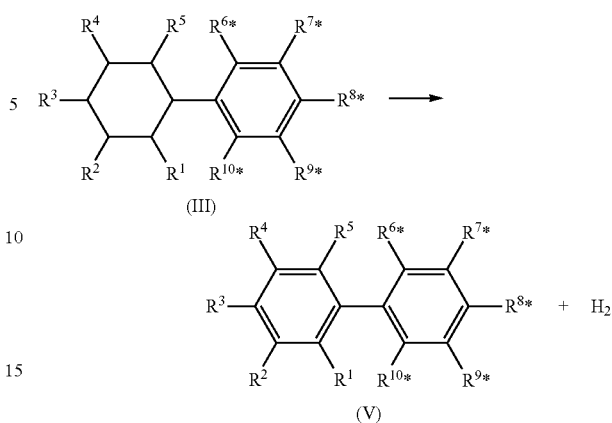

In formula (V), each $R^1$, $R^2$, $R^3$, $R^4$, and $R^5$ is defined as it was previously defined with respect to formula (I); and each $R^{6*}$, $R^{7*}$, $R^{8*}$, $R^{9*}$, and $R^{10*}$ likewise is defined as it was previously defined with respect to formula (II).

The dehydrogenation is conveniently conducted at a temperature from about 200° C. to about 600° C. and a pressure from about 100 kPa to about 3550 kPa (atmospheric to about 500 psig) in the presence of a dehydrogenation catalyst. A suitable dehydrogenation catalyst comprises one or more elements or compounds thereof selected from group 10 of the Periodic Table of the Elements, for example Pt, on a support, such as silica, alumina, or carbon. In one embodiment, the group 10 element is present in amounts from about 0.1 to about 5 wt % of the catalyst. Suitable dehydrogenation catalysts of some embodiments may further include tin (e.g., in amounts from about 0.01 to about 2 wt % of the catalyst, if present).

The result of the transalkylation followed by dehydrogenation is a biphenyl compound with selective substitution(s) on only one ring (or having all substitutions removed from only one ring). In this way, for instance, biphenyl compounds may be produced with unequal saturations (e.g., unequal number of substitutions) between the two phenyl rings of the biphenyl compounds.

Targeted Alkylation of Both Rings in Cyclohexylbenzyl and Biphenyl Compounds

In yet further embodiments, both rings of a cyclohexylbenzyl and/or biphenyl compound may be selectively alkylated in succession by using a combination of the above-described processes of transalkylation, dehydrogenation, and partial hydrogenation. Processes according to such embodiments may start with either of a cyclohexylbenzyl or a biphenyl compound (or a mixture thereof). For instance, processes according to some embodiments may include the following reactions (with each referenced formula as previously defined, unless noted otherwise):

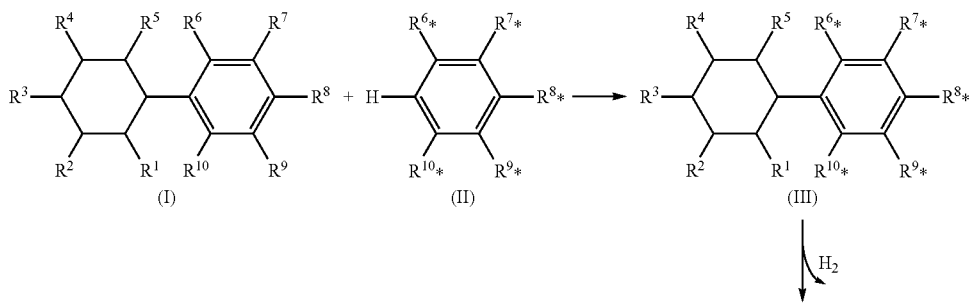

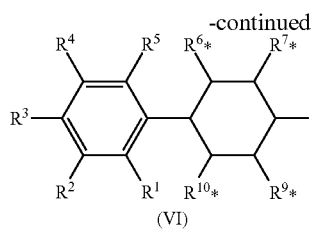

(VI)

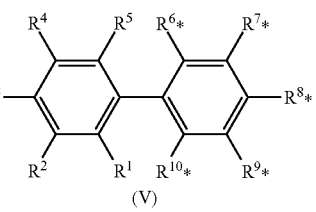

(V)

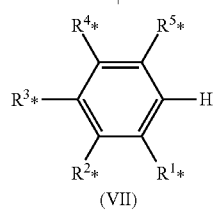

(VII)

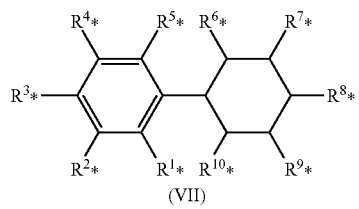

(VII)

Specifically, processes according to such embodiments include:

(i) Transalkylating a cyclohexylbenzyl compound according to formula (I) with a first substituted or unsubstituted benzene according to formula (II), thereby obtaining a first transalkylation reaction effluent comprising a transalkylated cyclohexylbenzyl compound according to formula (III) and positional isomers thereof, such that $R^1$-$R^5$ are bonded to the cyclohexyl ring of the transalkylated cyclohexylbenzyl compound;

(ii) Dehydrogenating the transalkylated cyclohexylbenzyl compound according to formula (III) to obtain a corresponding ring-replaced biphenyl compound of formula (V) (and optionally, positional isomers thereof that correspond to any positional isomers of formula (III) present in the first transalkylation reaction effluent, in which $R^1$-$R^5$ are bonded to the cyclohexyl ring of formula (III));

(iii) Partially hydrogenating the first biphenyl compound of formula (V) to obtain a partial hydrogenation reaction effluent comprising a ring-replaced cyclohexylbenzyl compound of formula (VI) (and positional isomers thereof), such that the $R^1$-$R^5$ groups of formula (VI) are bonded to the phenyl ring of formula (VI); and (iv) Transalkylating the ring-replaced cyclohexylbenzyl compound of formula (VI) with a second substituted or unsubstituted benzene according to formula (VII) (which may be either the same as, or different than, the first substituted or unsubstituted benzene), thereby obtaining a double ring-replaced cyclohexylbenzyl compound according to the structural formula (VIII).

In processes according the above-described embodiments, $R^{1*}$, $R^{2*}$, $R^{3*}$, $R^{4*}$, and $R^{5*}$ (e.g., in formulas VII and VIII) are each independently selected from the group consisting of H and $C_1$-$C_{10}$ alkyl, preferably aliphatic alkyl, provided that at least one of the following is true: $R^{1*}$ is not the same as $R^1$, $R^{2*}$ is not the same as $R^2$, $R^{3*}$ is not the same as $R^3$, and $R^{4*}$ is not the same as $R^4$. Any one or more of $R^{1*}$-$R^{5*}$ may in some embodiments be the same or different from any one or more of $R^{6*}$-$R^{10*}$.

Furthermore, both transalkylation steps (i) and (iv) according to processes of the above embodiments may take place over the same catalyst composition (e.g., using a recycle loop to provide the ring-replaced cyclohexylbenzyl compound of formula (VI) to the same reaction zone in which the first transalkylation (i) takes place). Alternatively, each transalkylation may take place over different catalyst compositions (which may be, but need not be, identical to each other), e.g., in two different reaction zones.

Processes according to certain embodiments may optionally further include dehydrogenating the double ring-replaced cyclohexylbenzyl compound of structural formula (VIII) so as to obtain a double ring-replaced biphenyl compound according to formula (IX) below, where each $R^{1*}$-$R^{10*}$ is as defined previously with respect to formulas (II) and (VII).

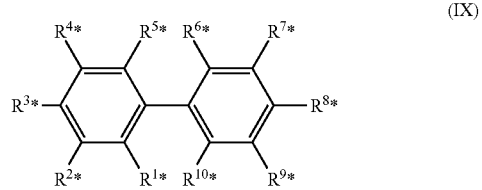

(IX)

Further, it should be noted that according to some embodiments, such processes optionally begin with a precursor biphenyl compound which is dehydrogenated to give the cyclohexylbenzyl compound of formula (I).

One specific example of processes of targeted alkylation of both rings of cyclohexylbenzyl and/or biphenyl compounds is the formation of dimethylbiphenyl by successive steps of trans alkylation-dehydrogenation-partial hydrogenation-transalkylation-dehydrogenation according to the following process, which starts with a step of hydroalkylation to obtain the cyclohexylbenzyl starting compound:

(i) Hydroalkylating benzene and hydrogen in the presence of a hydroalkylation catalyst under hydroalkylation conditions effective to produce a hydroalkylation reaction effluent comprising cyclohexylbenzene;

(ii) Transalkylating (1) at least a portion of the first hydroalkylation reaction effluent and (2) toluene in the presence of a transalkylation catalyst under transalkylation conditions effective to produce a transalkylation reaction effluent comprising one or more positional isomers of (cyclohexyl)toluene;

(iii) Dehydrogenating at least a portion of the transalkylation reaction effluent in the presence of a dehydrogenation catalyst under conditions effective to dehydrogenate at least a portion of the one or more positional isomers of (cyclohexyl)toluene to one or more corresponding positional isomers of methylbiphenyl;

(iv) Partially hydrogenating at least a portion of the methylbiphenyl so as to obtain one or more positional isomers of (methylcyclohexyl)benzene;

(v) Transalkylating the (methylcyclohexyl)benzene with additional toluene, thereby obtaining one or more positional isomers of (methylcyclohexyl)toluene;

(vi) Dehydrogenating the (methylcyclohexyl)toluene to obtain one or more corresponding positional isomers of dimethylbiphenyl (DMBP).

As with the more general processes of some embodiments, the transalkylation (v) above may take place in the same reaction zone (e.g., over the same transalkylation catalyst) as the transalkylation (ii). That is, at least a portion of the (methylcyclohexyl)benzene formed via the dehydrogenation (iv) may be recycled back to the same reaction zone in which the transalkylation (ii) takes place. Likewise, both dehydrogenation steps (iv) and (vi) may take place in the same dehydrogenation reaction zone. Thus, a process according to some such embodiments may be carried out in a system as illustrated in FIG. 1, where benzene is fed to a hydroalkylation reaction zone 100, forming a hydroalkylation effluent comprising CHB, which is taken via line 105 to a transalkylation reaction zone 110. Toluene is delivered to the transalkylation reaction zone 110 either directly or, as shown in FIG. 1, by combination with the CHB in feed line 105, prior to transalkylation. In addition, a recycle stream comprising methylcyclohexylbenzene is delivered to the transalkylation reaction zone 110 via second recycle line 135, such that the transalkylation feed includes (i) CHB; (ii) toluene; and (iii) recycled methylcyclohexylbenzene. The transalkylation reaction effluent carried out in line 115 therefore comprises cyclohexyltoluene, methylcyclohexyltoluene, and benzene (removed from CHB and methylcyclohexylbenzene upon transalkylation to form cyclohexyltoluene and MCHT, respectively). The benzene may readily be separated via a separation system 150 (which may be, e.g., one or more fractionation columns or other suitable separation device(s)) and recycled to the hydroalkylation reaction zone 100 as additional hydroalkylation feed, as shown in line 155. The MCHT and cyclohexyltoluene of the transalkylation reaction effluent, meanwhile, are delivered via line 156 to a dehydrogenation reaction zone 120, whereupon each is dehydrogenated to DMBP and methylbiphenyl, respectively, which are carried away along with hydrogen via line 125. A second separation system 160 (again, comprising one or more fractionation columns or other suitable separation device(s)) divides the effluent into: (i) a hydrogen-containing stream for recycle via line 165 to the hydroalkylation reaction zone 100; (ii) a product line 166 rich in the desired end-product DMBP; and (iii) a first recycle line 167 carrying a stream rich in methylbiphenyl. The first recycle line 167 brings the methylbiphenyl-rich stream to a hydrogenation reaction zone 130, whereupon the methylbiphenyl is partially hydrogenated to methylcyclohexylbenzene, which, as discussed above, is delivered via second recycle line 135 to the transalkylation reaction zone 110. Additional hydrogen for the hydrogenation reaction may be delivered directly to the hydrogenation zone 130 or, as shown in FIG. 1, mixed with the methylbiphenyl feed in line 167. In some embodiments, at least a portion of the hydrogen leaving the second separation system 160 (e.g., via line 165) may be routed to the hydrogenation reaction zone 130 (not shown in FIG. 1).

Processes according to the above description for forming DMBP offers an advantageous alternative to forming DMBP by hydroalkylation of toluene. It is believed that steric forces involved in the transalkylation reaction mechanism hinder the formation of undesirable 2,X' positional isomers of DMBP (where X' is 2, 3, or 4, i.e., where any one or more of the methyl groups is on the 2-position of either phenyl ring).

In some embodiments, overall benzene consumption in such processes may be nearly zero, as it is expected that: (1) any benzene byproduct produced during transalkylation may be recycled as additional hydroalkylation feed; (2) any byproduct cyclohexylbenzenes that consume byproduct benzene during the transalkylation steps may similarly be recycled as additional feed to the first transalkylation (ii); and finally, (3) any cyclohexane byproduct of the hydroalkylation reaction (e.g., resulting from complete hydrogenation of benzene during that reaction) may be dehydrogenated to benzene to provide further hydroalkylation feed, for instance as described in U.S. Pat. No. 8,247,627, column 7, line 35 through column 9, line 30.

In yet further embodiments, xylene could be used for either or both transalkylation steps instead of or in addition to toluene. That is, some embodiments include transalkylation with an alkylbenzene selected from the group consisting of toluene, xylene, and mixtures thereof. In such cases, the transalkylation reaction effluent in (ii) will comprise one or more positional isomers of (cyclohexyl)alkylbenzenes selected from the group consisting of (cyclohexyl)toluene, (cyclohexyl)xylene, and mixtures thereof (provided that the positional isomers are such that the methyl group is on the phenyl ring of each of the (cyclohexyl)alkylbenzenes); and the dehydrogenation (iii) will result in one or more positional isomers of alkyl-biphenyl compounds selected from the group consisting of: (1) one or more positional isomers of methylbiphenyl; (2) 2,3-dimethylbiphenyl; (3) 2,4-dimethylbiphenyl; (4) 3,4-dimethylbiphenyl; and mixtures of any two or more of the foregoing.

As can be seen, at this point in the process, where xylenes are used in the transalkylation, at least some of the alkyl-biphenyl compounds are positional isomers of DMBP in which both methyl groups are on the same phenyl ring (e.g., compounds 2, 3, and 4). Thus, such compounds can be withdrawn as DMBP with unequal saturations between its two phenyl rings.

Optionally, the process could continue (as already demonstrated with respect to transalkylations involving toluene, above). In embodiments wherein the process continues with the use of xylenes in transalkylation, the alkyl-biphenyl compounds can be partially hydrogenated to provide an (alkylcyclohexyl)benzene selected from the group consisting of one or more positional isomers of (methylcyclohexyl)benzene; one or more positional isomers of (dimethylcyclohexyl)benzene; and mixtures thereof; the (alkylcyclohexyl)benzene may then be transalkylated with an additional alkylbenzene selected from the group consisting of toluene, xylene, and mixtures thereof, so as to obtain an (alkylcyclohexyl)alkylbenzene, which is then dehydrogenated to obtain a polyalkylbiphenyl compound selected from the group consisting of: one or more positional isomers of dimethylbiphenyl; one or more positional isomers of trimethylbiphenyl (in which two methyl groups are on one phenyl ring, and one methyl group on the other phenyl ring, of the trimethylbiphenyl); one or more positional isomers of tetramethylbiphenyl (in which two methyl groups are present on each phenyl ring); and mixtures of any two or more of the foregoing.

Combined Hydroalkylation and Transalkylation

As noted previously, cyclohexylbenzyl compounds such as cyclohexylbenzene and (methylcyclohexyl)toluene (MCHT) are conveniently formed by hydroalkylation. Thus, the processes described herein may form at least a portion of the treatment of a hydroalkylation reaction effluent to obtain desired selective alkylations (and/or to selectively remove undesired substitutions).

Advantageously, according to some embodiments, the transalkylation process may be combined with the hydroalkylation process, by utilization of a bifunctional catalyst (e.g., a catalyst capable of catalyzing both hydroalkylation and transalkylation), or of a multi-catalyst reactor zone.

Suitable bifunctional catalysts include a hydrogenation component (e.g., any hydrogenation metal discussed previously herein) and a solid acid alkylation component, typically a molecular sieve. Suitable bifunctional catalysts for use in such hydroalkylation/transalkylation reactions comprise a hydrogenation component (e.g., a hydrogenation metal selected from group 10 of the Periodic Table of the Elements, with palladium being particularly advantageous) and a solid acid alkylation component, typically a molecular sieve. The catalyst may also include a binder such as clay, silica and/or metal oxides. In general, suitable bifunctional catalysts include the hydroalkylation catalysts described in Paragraphs [0025]-[0029] of WIPO Publication No. 2014/159104 (published 2 Oct. 2014, with International Filing Date of 7 Mar. 2014), which is incorporated by reference herein.

One example bifunctional catalyst, as described in WIPO Publication No. 2014/159104, comprises a molecular sieve of the MCM-22 family. Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in EP 0 293 032), ITQ-1 (described in U.S. Pat. No. 6,077,498), ITQ-2 (described in WO 97/17290), MCM-36 (described in U.S. Pat. No. 5,250,277), MCM-49 (described in U.S. Pat. No. 5,236,575), MCM-56 (described in U.S. Pat. No. 5,362,697) and mixtures thereof.

A preferred bifunctional catalyst according to yet further embodiments is a Pd/USY catalyst (i.e., where the hydrogenation component is Pd at about 0.1 to about 2% Pd (such as about 0.3% Pd) by weight of the catalyst, and the molecular sieve is USY). The USY in some embodiments is bound with an $Al_2O_3$ binder material in a combined composition, such that the bound molecular sieve comprises 80 wt % USY and 20 wt % $Al_2O_3$. In alternative embodiments, the bound molecular sieve comprises from about 60 wt % to about 90 wt % USY, and from about 10 to about 40 wt % $Al_2O_3$, based on the weight of the bound molecular sieve. Furthermore, in certain embodiments, adjusting the ratio of silica to alumina (sometimes shorthanded herein to "$Si/Al_2$") in the molecular sieve of the catalyst results in adjusting the selectivity of the catalyst to transalkylation vs. hydroalkylation reaction products. In particular, in some embodiments, a higher $Si/Al_2$ ratio leads to a greater selectivity to transalkylation products, while a lower $Si/Al_2$ ratio leads to a greater selectivity to hydroalkylation products. In this way, bifunctional catalysts can be tailored and/or adjusted to obtain a desired balance between hydroalkylation and transalkylation in a combined reaction. In further embodiments, hydrogenation metal concentration, acidity (e.g., metal concentration vs. $Si/Al_2$ ratio), zeolite:binder ratio, and binder type may also be adjusted in order to modify the balance between hydroalkylation and transalkylation products.

Typically, hydroalkylation of aromatics to form cycloalkylaromatics involves a feed including hydrogen and substituted or unsubstituted benzene (such as benzene, toluene, xylene, and mixtures thereof). The process is described in detail in Paragraphs [0025]-[0047] of US 2014/0275605, the entirety of which is incorporated by reference herein. In summary, the substituted or unsubstituted benzene is partially hydrogenated to the corresponding cycloalkenyl, which in turn undergoes an alkylation reaction with additional benzene (and/or toluene and/or xylene). Processes of combined hydroalkylation and transalkylation according to some embodiments of the present invention involve the addition of a cyclohexylbenzyl compound and/or a biphenyl compound to the typical hydroalkylation feed. The substituted or unsubstituted benzene in the feed will either undergo hydroalkylation (as summarized above), or will undergo transalkylation with a cyclohexylbenzyl compound in the feed (thereby replacing the phenyl ring of such compound, as described previously herein), catalyzed in a manner similar to the alkylation portion of the hydroalkylation reaction. The cyclohexylbenzyl compound in the feed is either added directly (as just noted), and/or results from partial hydrogenation of a biphenyl compound in the feed (catalyzed by the hydrogenation component of the bifunctional catalyst).

Accordingly, processes of combined hydroalkylation and transalkylation may, in some embodiments, include providing a hydroalkylation feed comprising, as shown in the structural formulas below, a substituted or unsubstituted benzene according to formula (II) (with each R group defined as set forth previously), hydrogen, and one or both of a cyclohexylbenzyl compound according to formula (I) (also with R groups as previously defined) and a biphenyl compound according to formula (IV) (also with R groups as previously defined), which may be labeled a "precursor biphenyl."

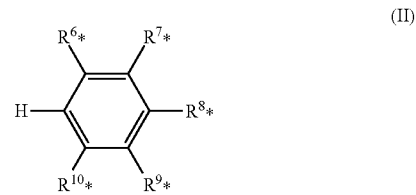

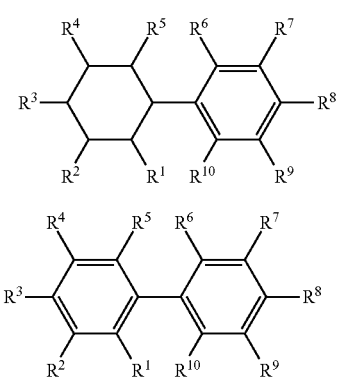

The feed is contacted with a bifunctional catalyst comprising a hydrogenation component and a solid acid alkylation component such as a molecular sieve, leading to formation of a reaction effluent comprising a hydroalkylation product and a transalkylation product. The hydroalkylation product has the formula (X) (and positional isomers thereof), where each of $R^{6*}$, $R^{7*}$, $R^{8*}$, $R^{9*}$, and $R^{10*}$ is as defined for the substituted or unsubstituted benzene of formula (II) (i.e., each $R^{6*}$-$R^{10*}$ is independently selected from the group consisting of H and $C_1$-$C_{10}$ solid alkyl groups, preferably non-aliphatic alkylation groups, provided that one or more of the following is true, with respect to the $R^6$-$R^{10}$ of formula (I): $R^{6*}$ is different from $R^6$, $R^{7*}$ is different from $R^7$, $R^{8*}$ is different from $R^8$, $R^{9*}$ is different from $R^9$, and $R^{10*}$ is different from $R^{10}$). The transalkylation product if according to the formula (III) and positional isomers thereof, according to transalkylation embodiments previously discussed (and with R groups as previously defined).

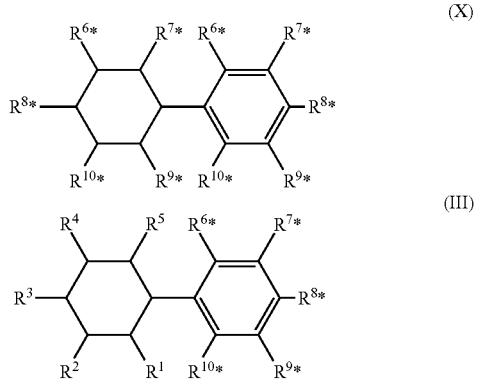

In some embodiments, the combined hydroalkylation and transalkylation process may be part of an integrated process to form an alkylbiphenyl, such as DMBP, which may in turn be used for, e.g., the formation of plasticizers. For example, a process as shown in FIG. 1 and previously discussed could combine the hydroalkylation reaction zone 100 and transalkylation reaction zone 110 into a single combined hydroalkylation and transalkylation reaction zone, and otherwise maintain the same process streams shown in FIG. 1.

As another example, as discussed previously, the transalkylation reaction can advantageously provide a means to eliminate or at least reduce the number of undesirable positional isomers of (methylcyclohexyl)toluene (MCHT) and/or DMBP in a process for the formation of DMBP via hydroalkylation. Such processes include hydroalkylation of toluene to form positional isomers of MCHT, and dehydrogenation of the MCHT to DMBP, and are discussed, e.g., in US 2014/0275605. Rather than conducting a separate transalkylation to eliminate or reduce unwanted positional isomers (e.g., the 2,X' isomers of MCHT in the hydroalkylation reaction effluent and/or the 2,X' isomers of DMBP in the dehydrogenation reaction effluent, where X' is 2', 3', or 4'), the unwanted positional isomers may be separated from the MCHT and/or DMBP and recycled back to the hydroalkylation reaction. Where a bifunctional catalyst is employed in the hydroalkylation reaction, the undesired isomers will advantageously undergo transalkylation reactions with toluene in the feed, thereby at least reducing the amount of the undesired isomers.

Thus, processes according to some embodiments may include contacting a bifunctional catalyst comprising a hydrogenation component and a molecular sieve with a hydroalkylation feed. The hydroalkylation feed comprises toluene, hydrogen, and one or both of MCHT and DMBP, wherein n wt % of the MCHT and/or DMBP (based on the combined weight of MCHT and DMBP in the feed) comprises 2,X' positional isomers of MCHT and/or DMBP (i.e., positional isomers in which at least one methyl group is in the 2-position on either ring of said MCHT and/or DMBP). The contacting results in a reaction effluent comprising a hydroalkylation product and a transalkylation product. The hydroalkylation product comprises one or more positional isomers of MCHT. Further, the transalkylation product also comprises one or more positional isomers of MCHT. However, the transalkylation product comprises only m wt % of 2,X' positional isomers of MCHT, where m is less than n.

In yet further embodiments, as noted previously, a multiple catalyst reactor zone may be employed, such that in any of the aforementioned combined processes, two or more catalysts serving different functions are used instead of, or in addition to, a bifunctional catalyst. For instance, a reactor zone for combined hydroalkylation and transalkylation may comprise a hydrogenation catalyst and an alkylation catalyst (which may serve both alkylation and transalkylation functions). Suitable hydrogenation catalysts may include any hydrogenation metal (e.g., a metal selected from group 10 of the Periodic Table of the Elements). One example of a hydrogenation catalyst according to some embodiments includes S—Ni, a selective hydrogenation catalyst to turn biphenyl to CHB, although any other hydrogenation catalyst may be utilized. Suitable alkylation catalysts may comprise a molecular sieve, such as any of the molecular sieves discussed previously with respect to bifunctional catalysts. In yet further embodiments, the multiple catalysts may comprise a hydroalkylation catalyst (e.g., a catalyst comprising a hydrogenation component and an MCM-22 molecular sieve) and a transalkylation catalyst (e.g., comprising a zeolite Y and/or zeolite beta molecular sieve).

The multiple catalysts may be disposed in the reaction zone as a mixed bed, stacked bed, or the like. Some embodiments include a mixed bed comprising two or more catalysts, and having a concentration gradient of at least one of the catalysts. That is, the catalyst composition can be tailored as a function of position in the reactor. For instance, the mixed catalyst bed of some embodiments may include a hydrogenation (and/or hydroalkylation) catalyst such that the concentration of hydrogenation (hydroalkylation) catalyst in the mixed bed becomes more dilute as a function of bed length (with dilution of the hydrogenation and/or hydroalkylation catalyst increasing in the downstream direction along the length of the mixed bed). This may provide rapid initial hydroalkylation, and, as more cyclohexylbenzyl hydroalkylation products are formed, the lower hydrogenation and/or hydroalkylation catalyst concentration farther along the catalyst bed helps to slow dialkylate formation and full hydrogenation to bicyclohexyl compounds.

A similar concept can further be applied to a catalyst bed comprising bifunctional catalyst, wherein the hydrogenation metal loading on the bifunctional catalyst is configured to follow a similar concentration gradient, with increased metal loading in the upstream portion of the bed, and progressively lower metal loading in the downstream direction of the bed. This would have a similar effect of increased hydrogenation/hydroalkylation in the initial stages of reaction, with decreased formation of the dialkylated products and/or fully hydrogenated bicyclohexyl products as the reaction progresses.

EXPERIMENTAL

The invention will now be more particularly described with reference to the following non-limiting Examples. Unless otherwise indicated, room or ambient temperature is about 23° C.

Example 1: Cyclohexylbenzene Transalkylation with Various Alkyl Aromatics

The experiments discussed in Example 1 utilized a reactor unit with 8 parallel reactors heated by furnace. For different tests, anywhere from 1-8 reactors were utilized. The reactors consisted of quartz tubes of 9 mm inner diameter. Annular $N_2$ flow on the outside of the quartz reactor allowed for pressure equilibrium between the inside and outside of each reactor channel. Catalyst extrudates (consisting of USY zeolite on alumina binder) were crushed to 20/40 mesh loaded in quantities of 2 g after being diluted up to 4 g in crushed quartz. A quartz wool plug was used at the top and bottom of the catalyst bed to keep catalyst in place. Two sets of 4 parallel reactors were placed in heated furnaces to control isothermal reaction temperature. Each reactor contained an internal thermocouple in the catalyst bed in a 1/16" thermowell. The reactors were topped off with the same quartz chips.

The catalysts in all reactors were pre-conditions in situ as described in subsequent examples. An ISCO syringe pump was used to introduce feed to the reactor system. The feed was pumped through a vaporizer before being mixed inline with $N_2$ at a molar ratio of about 0.7 (gas to hydrocarbon liquid).

As shown in Table 1 below, 3 different liquid hydrocarbon feeds were used:

(1-a) 66 wt % toluene and 34 wt % cyclohexylbenzene (CHB) delivered at a liquid pump rate corresponding to a WHSV (weight hourly space velocity, on basis of catalyst in the reactor) of 1 $hr^{-1}$.

(1-b) 57 wt % mixed xylenes and 33 wt % CHB delivered at a liquid pump rate corresponding to a WHSV of 1 $hr^{-1}$. The mixed xylenes comprised 18 wt % ethylbenzene, 22 wt % p-xylene; 48 wt % m-xylene; and 12 wt % o-xylene.

(1-c) 67 wt % ethylbenzene and 33 wt % CHB.

Samples were analyzed on an Agilent 7890 GC equipped with a 5975C MSD detector and FID and an automatic liquid sampler (ALS). Typical injection size for analysis was about 0.5 µl.

Results of the reaction are shown in Table 1 below.

TABLE 1

Experimental Results of Example 1 CHB Transalkylations

| Co-Feed | Toluene (1-a) | Mixed Xylenes (1-b) | Ethylbenzene (1-c) |
|---|---|---|---|
| Temperature (° C.) | 175 | 165 | 165 |
| Pressure (kPag) | 1137.6 | 1137.6 | 1137.6 |
| CHB conversion (%) | 73% | 43% | 40% |
| Desired product | (cyclo-hexyl)toluene | (cyclo-hexyl)xylene | (cyclo-hexyl)ethylbenzene |
| [g desired product]/[g total] | 19% | 7% | 13% |

The results show that the proposed reaction pathway is viable, and may readily be optimized and combined with downstream separations and recycles to improve overall process yields.

Example 2: Further Cyclohexylbenzene Transalkylation with Toluene

The transalkylation test of Example 2 was carried out in a fixed bed down-flow reactor. The reactor was ½ inch (1.27 cm) inner diameter. The catalyst used in the study was a commercial catalyst consisting of USY zeolite on alumina binder. The catalyst charge was 1.65 g, and the catalyst was activated by heating up the catalyst bed to 260° C., and then holding at that temperature for 8 hours. Hydrogen flow rate was 50 cc/minute. Reactor pressure was maintained constant, at 50 psig (344.7 kPag) throughout catalyst activation.

The feed used in the transalkylation test was prepared by physically blending anhydrous toluene purchased from Sigma Aldrich and cyclohexylbenzene purchased from Alfa Aesar in the ratio of 83:17 by weight. The transalkylation test was carried out at 180° C. Reactor pressure, WHSV, and hydrogen/hydrocarbon molar ratio were kept constant at 200 psig (1379.0 kPag), 2.5 $hr^{-1}$, and 0.7, respectively.

Samples were analyzed on an Agilent 7890 GC equipped with a 5975 mass spectrometer detector and Flame ionization detector. Dual injection of a 0.5 µl sample size was utilized for two independent identical columns, one for FID and the other for MS (mass spec) detector. The carbon number of components greater than or equal to $C_{12}$ was inferred from molecular weights obtained from the MS result.

It was found that the feed contained 83.33 wt % toluene and 16.67 wt % cyclohexylbenzene. The reaction produced (cyclohexyl)toluene and other byproducts. The effluent contained: 3.6 wt % benzene; 80.6 wt % toluene; 7.3 wt % cyclohexylbenzene; 7.0 wt % cyclohexyl(toluene), and 1.5 wt % heavies ($C_{12}$ or greater). Thus, the viability of the transalkylation route to effectively methylate only the phenyl ring of CHB is demonstrated, and offers an attractive alternative to other CHB alkylation options (such as methanol addition to the aromatic).

Example 3: Combined Hydrogenation, Hydroalkylation, and Transalkylation

Biphenyl spiked experiments (e.g., feed comprising hydrogen, toluene, and biphenyl) were run in order to assess the feasibility to hydrogenate and transalkylate biphenyl type molecules directly inside a hydroalkylation reactor. Catalytic performance tests described in this example were carried out in a 7 mm diameter×150 mm isothermal reactor, equipped with a 1.6 mm internal thermowell for temperature monitoring.

Two different catalysts, both having 0.30 wt % Pd on a bound molecular sieve support comprising 80 wt % USY and 20 wt % $Al_2O_3$, were used: (1) catalysts with $Si/Al_2$ ratio in the bound molecular sieve of 7, and (2) those with $Si/Al_2$ ratio in the molecular sieve of 30. About 2 g of catalyst, sized to 0.4-0.6 mm particles, was diluted with amorphous silicon carbide and loaded into the reactor tube. Testing conditions were at a WHSV of 2 $h^{-1}$ (on a total liquid feed basis) at 140° C. and 11 barg (1100 kPag).

The $H_2$ and toluene/biphenyl feed were mixed using a high efficiency static mixer and the $H_2$: toluene molar ratio was maintained at 2. The feed consisted of either pure toluene or 89.6 wt % toluene and 10.4 wt % biphenyl, as indicated in Table 3 below (where "Biphenyl Added" value of "Y" indicates additional of biphenyl, so as to make the feed 89.6 wt % toluene and 10.4 wt % biphenyl).

Liquid samples were collected from the reactor effluent at process pressure. Analysis of the liquid samples was performed on an Agilent 7890 GC equipped with an autosampler and 150 vial sample tray.

The expected reactions included hydrogenation of the biphenyl in the feed to cyclohexylbenzene, and transalkylation of the cyclohexylbenzene with toluene in the feed to form (cyclohexyl)toluene and benzene. Benzene can react further to form cyclohexane (via hydrogenation), cyclohexylbenzene (via hydroalkylation with hydrogen and additional benzene), and additional (cyclohexyl)toluene (via hydroalkylation with hydrogen and toluene). Thus, in theory, one mole of biphenyl can potentially yield two moles of (cyclohexyl)toluene in this process. In addition, the expected reactions also included hydroalkylation of two toluenes to the $C_{14}$ species (methylcyclohexyl)toluene (MCHT).

As shown in Table 3, for both compositions of catalyst used, the addition of biphenyl resulted in a drop in toluene conversion. Depending on the catalyst, the overall (toluene and biphenyl) conversion either dropped or remained constant before and after biphenyl addition. Relative transalkylation and hydroalkylation rates depended strongly on the applied $Si/Al_2$ ratio of the applied catalysts. For the highest $Si/Al_2$ catalyst, the majority of the formed $C_{13}$ and $C_{14}$ transalkylation and hydroalkylation products consisted of the transalkylation product (i.e., the $C_{13}$ species (cyclohexyl) toluene). For the lowest $Si/Al_2$, on the other hand, the majority of the formed $C_{13}$ and $C_{14}$ species was the $C_{14}$ hydroalkylation product (MCHT). This suggests that selectivity between hydroalkylation and transalkylation in a combined reaction may be controlled in part by the $Si/Al_2$ ratio of the molecular sieve.

TABLE 3

Results of combined hydrogenation, hydroalkylation, and transalkylation

| Run | 3-a | 3-b | 3-c | 3-d |
|---|---|---|---|---|
| Catalyst $Si/Al_2$ Ratio | 7 | 7 | 30 | 30 |
| Biphenyl Added? | N | Y | N | Y |
| Toluene Conversion (wt %) | 30.4 | 8.0 | 25.6 | 19.0 |
| Biphenyl Conversion (wt %) | — | 95.8 | — | 100.0 |
| Overall Conversion (wt %) | 30.4 | 17.2 | 25.6 | 27.5 |

TABLE 3-continued

Results of combined hydrogenation, hydroalkylation, and transalkylation

| | Run | 3-a | 3-b | 3-c | 3-d |
|---|---|---|---|---|---|
| Select invities (% of converted feed) | Cyclohexane | — | 0.3 | — | 0.2 |
| | Methylcyclohexane | 48.5 | 24.7 | 47.0 | 47.2 |
| | Benzene | — | 0.8 | — | 0.4 |
| | Dimethylbicylohexane | 0.9 | — | 1.1 | — |
| | Bicyclohexane | — | 1.2 | — | 2.8 |
| | Cyclohexylbenzene | — | 43.7 | — | 41.3 |
| | $C_{13}$ transalkylate ((cyclohexyl)toluene) | — | 7.9 | — | 16.5 |
| | $C_{14}$ hydroalkylate (MCHT) | 49.7 | 20.9 | 50.9 | 9.2 |
| | $C_{15}+$ | 0.2 | 0.0 | 0.4 | 0.9 |
| | Unidentified species | 0.7 | 0.5 | 0.6 | 0.3 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention. All documents described herein are incorporated by reference herein, including any priority documents and/or testing procedures to the extent they are not inconsistent with this text. Likewise, the term "comprising" is considered synonymous with the term "including" for purposes of Australian law and whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa.

What is claimed is:

1. A process for forming cyclohexylbenzyl and/or biphenyl compounds, the process comprising:

(a) contacting a first cyclohexylbenzyl compound with a substituted or unsubstituted benzene in the presence of a transalkylation catalyst, thereby obtaining a transalkylated cyclohexylbenzyl compound, wherein the transalkylation catalyst comprises a solid acid catalyst;

wherein the first cyclohexylbenzyl compound has the structural formula (I)

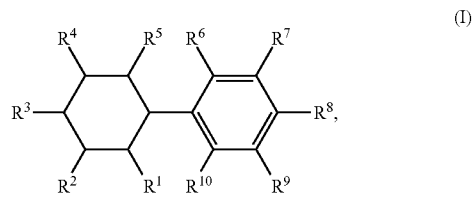

where each $R^1$-$R^{10}$ is independently H or a $C_1$-$C_{10}$ alkyl group;

wherein the substituted or unsubstituted benzene has the structural formula (II)

(II)

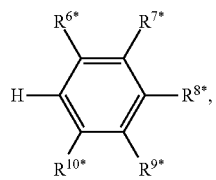

where each $R^{6*}$-$R^{10*}$ is independently H or a $C_1$-$C_{10}$ alkyl group, and further provided that one or more of the following is true: $R^{6*}$ is different from $R^6$, $R^{7*}$ is different from $R^7$, $R^{8*}$ is different from $R^8$, $R^{9*}$ is different from $R^9$, and $R^{10*}$ is different from $R^{10}$; and wherein the transalkylated cyclohexylbenzyl compound has the structural formula (III)

(III)

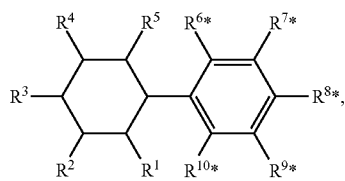

or a positional isomer thereof in which the cyclohexyl ring has each $R^1$-$R^5$ covalently bonded thereto, and the phenyl ring has each $R^{6*}$-$R^{10*}$ covalently bonded thereto.

2. The process of claim 1, further comprising partially hydrogenating a precursor biphenyl compound having the structural formula (IV)

(IV)

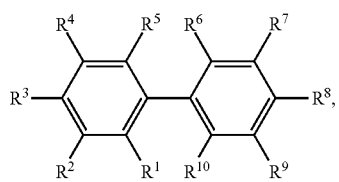

thereby obtaining the first cyclohexylbenzyl compound contacted with the substituted or unsubstituted benzene in (a).

3. The process of claim 2, further comprising:

(a) dehydrogenating the transalkylated cyclohexylbenzyl compound to obtain a ring-replaced biphenyl compound having the structural formula (V)

(V)

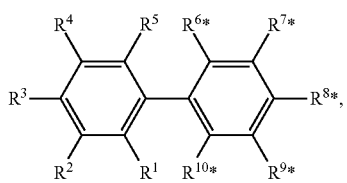

or a positional isomer thereof in which one phenyl ring has each $R^1$-$R^5$ covalently bonded thereto, and the other phenyl ring has each $R^{6*}$-$R^{10*}$ covalently bonded thereto;

(b) partially hydrogenating the ring-replaced biphenyl compound in the presence of a hydrogenation catalyst to obtain a ring-replaced cyclohexylbenzyl compound having the formula (VI)

(VI)

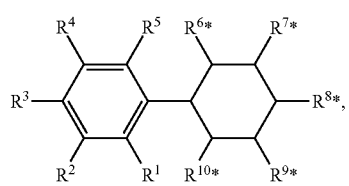

or a positional isomer thereof in which the phenyl ring has each $R^1$-$R^5$ covalently bonded thereto, and the cyclohexyl ring has each $R^{6*}$-$R^{10*}$ covalently bonded thereto;

(c) and contacting the ring-replaced cyclohexylbenzyl compound with an additional substituted or unsubstituted benzene in the presence of a second transalkylation catalyst, thereby obtaining a further transalkylated cyclohexylbenzyl compound, wherein the additional substituted or unsubstituted benzene has the structural formula (VII)

(VII)

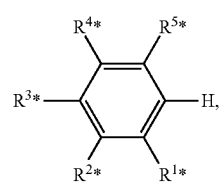

or a positional isomer thereof, where any one of $R^{1*}$-$R^{5*}$ is a $C_1$-$C_{10}$ alkyl group, and the rest of $R^{1*}$-$R^{5*}$ are each independently selected from H and $C_1$-$C_{10}$ alkyl groups, and further provided that one or more of the following is true: $R^{1*}$ is different from $R^1$, $R^{2*}$ is different from $R^2$, $R^{3*}$ is different from $R^3$, $R^{4*}$ is different from $R^4$, and $R^{5*}$ is different from $R^5$; and wherein the further transalkylated cyclohexylbenzyl compound has the structural formula (VIII)

(VIII)

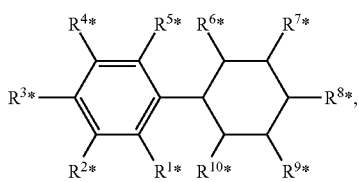

or a positional isomer thereof in which the phenyl ring has each $R^{1*}$-$R^{5*}$ covalently bonded thereto, and the cyclohexyl ring has each $R^{6*}$-$R^{10*}$ covalently bonded thereto.

4. The process of claim 3, further comprising dehydrogenating the further transalkylated cyclohyexylbenzyl compound in order to obtain a double ring-replaced biphenyl compound having the structural formula (IX)

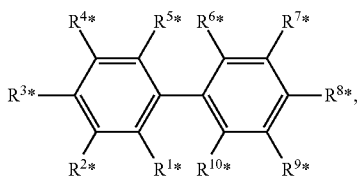
(IX)

or a positional isomer thereof in which one phenyl ring has each $R^{1*}$-$R^{5*}$ covalently bonded thereto, and the other phenyl ring has each $R^{6*}$-$R^{10*}$ covalently bonded thereto.

5. The process of claim 1, wherein $R^1$-$R^5$ are each H.

6. The process of claim 5, wherein $R^6$-$R^{10}$ are each H.

7. The process of claim 1, wherein one of $R^1$-$R^5$ is a $C_1$-$C_5$ alkyl group, and the rest of $R^1$-$R^5$ are each H; and further wherein $R^6$-$R^{10}$ are each H.

8. The process of claim 1, wherein the substituted or unsubstituted benzene and the additional substituted or unsubstituted benzene are each independently selected from the group consisting of toluene, xylene, and ethylbenzene.

9. The process of claim 1, wherein $R^{1*}$-$R^{5*}$ and $R^{6*}$-$R^{10*}$ each comprise the same five substitutions.

10. The process of claim 3, wherein the transalkylation catalyst and the second transalkylation catalyst are each independently selected from molecular sieves having a large pore molecular sieve having a Constraint Index less than 2.

11. The process of claim 3, wherein a single catalyst composition is both the transalkylation catalyst and the second transalkylation catalyst.

12. The process of claim 1, wherein:
the cyclohexylbenzyl compound is cyclohexylbenzene (CHB);
the substituted or unsubstituted benzene is a substituted benzene selected from the group consisting of toluene, xylene, ethylbenzene, and mixtures thereof; and
the transalkylated cyclohexylbenzyl compound comprises one or more isomers of cyclohexyltoluene, cyclohexylxylene, cyclohexylethylbenzene, or mixtures thereof, respectively.

13. A process for forming cyclohexylbenzyl and/or biphenyl compounds, the process comprising:
(a) providing to a combined hydroalkylation and transalkylation reaction zone a hydroalkylation feed comprising (i) hydrogen, (ii) a substituted or unsubstituted benzene, and (iii) one or both of a cyclohexylbenzyl compound and a precursor biphenyl compound;
wherein the combined hydroalkylation and transalkylation reaction zone comprises (A) a hydrogenation catalyst and an alkylation catalyst, or (B) a bifunctional catalyst comprising (i) a hydrogenation metal selected from group 10 of the Periodic Table of the Elements and (ii) a molecular sieve;
further wherein the substituted or unsubstituted benzene has the structural formula (II)

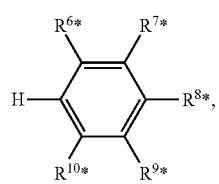
(II)

where any one of $R^{6*}$-$R^{10*}$ is a $C_1$-$C_{10}$ alkyl group, and the rest of $R^{6*}$-$R^{10*}$ are each independently selected from H and $C_1$-$C_{10}$ alkyl groups, and further provided that one or more of the following is true: $R^{6*}$ is different from $R^6$, $R^{7*}$ is different from $R^7$, $R^{8*}$ is different from $R^8$, $R^{9*}$ is different from $R^9$, and $R^{10*}$ is different from $R^{10}$;
further wherein the cyclohexylbenzyl compound has the structural formula (I)

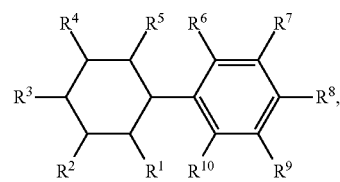
(I)

where each $R^1$-$R^{10}$ is independently H or a $C_1$-$C_{10}$ alkyl group; and
further wherein the precursor biphenyl compound has the structural formula (IV)

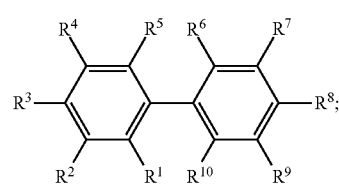
(IV)

and
(b) forming a reaction effluent comprising a hydroalkylation product and a transalkylation product, where the hydroalkylation product has the formula (X)

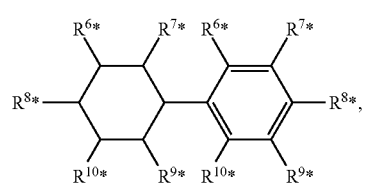
(X)

or a positional isomer thereof in which the cyclohexyl ring has one of each $R^{6*}$-$R^{10*}$ covalently bonded thereto, and the phenyl ring also has one of each $R^{6*}$-$R^{10*}$ covalently bonded thereto; and further where the transalkylation product has the formula (III)

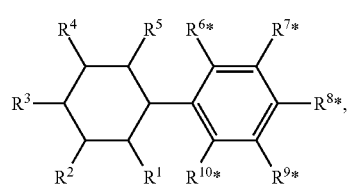
(III)

or a positional isomer thereof in which the cyclohexyl ring has each $R^1$-$R^5$ covalently bonded thereto, and the phenyl ring has each $R^{6*}$-$R^{10*}$ covalently bonded thereto.

14. The process of claim 13, wherein the substituted or unsubstituted benzene is selected from the group consisting of toluene, xylene, and ethylbenzene; and further wherein the cyclohexylbenzyl compound is selected from the group consisting of cyclohexylbenzene, (methylcyclohexyl)toluene, (dimethylcyclohexyl)xylene, (cyclohexyl)toluene, and mixtures thereof.

15. The process of claim 13, wherein:
the hydroalkylation feed comprises hydrogen, toluene, and either or both of methylcylohexyltoluene (MCHT) and dimethylbiphenyl (DMBP), such that n % by combined weight of the MCHT and DMBP in the feed is comprised of positional isomers in which one of the two methyl groups is in the 2-position on a phenyl ring of the MCHT or DMBP; and
further wherein the transalkylation product in the reaction effluent comprises MCHT, such that m % by weight of the MCHT in the reaction effluent is comprised of positional isomers in which one of the two methyl groups is in the 2-position on the phenyl ring of the MCHT, where m is less than n.

16. The process of claim 13, wherein the hydrogenation catalyst comprises a metal selected from the group consisting of Pd, Pt, Ni, Cu, and any combination thereof, and further wherein the alkylation catalyst is selected from the group consisting of (i) bound molecular sieves comprising USY zeolite and $Al_2O_3$, (ii) MCM-22 family molecular sieves, and (iii) any combination thereof.

17. The process of claim 13, wherein the hydrogenation metal of the bifunctional catalyst is Pd or Pt, and further wherein the molecular sieve of the bifunctional catalyst is a bound molecular sieve comprising USY zeolite and $Al_2O_3$.

18. The process of claim 17, wherein the bound molecular sieve of the bifunctional catalyst has a ratio of Si to $Al_2$ of about 7, and further wherein the reaction effluent comprises more hydroalkylation product than transalkylation product.

19. The process of claim 17, wherein the bound molecular sieve of the bifunctional catalyst has a ratio of Si to $Al_2$ of about 30, and further wherein the reaction effluent comprises more transalkylation product than hydroalkylation product.

20. A process for forming a polyalkylbiphenyl compound, the process comprising:
(a) hydroalkylating benzene and hydrogen in the presence of a hydroalkylation catalyst under hydroalkylation conditions effective to produce a hydroalkylation reaction effluent comprising cyclohexylbenzene;
(b) contacting (i) at least a portion of the hydroalkylation reaction effluent and (ii) an alkylbenzene selected from the group consisting of toluene, xylene, and mixtures thereof, with a transalkylation catalyst under conditions effective to produce a transalkylation reaction effluent comprising one or more isomers of a (cyclohexyl)alkylbenzene selected from the group consisting of (cyclohexyl)toluene and positional isomers thereof, (cyclohexyl)xylene and positional isomers thereof, and mixtures of any two or more of the foregoing, provided that the methyl group of any of said positional isomers of (cyclohexyl)toluene and/or (cyclohexyl)xylene is on the phenyl ring of the (cyclohexyl)toluene and/or (cyclohexyl)xylene;
(c) dehydrogenating at least a portion of the transalkylation reaction effluent in the presence of a dehydrogenation catalyst under conditions effective to dehydrogenate at least a portion of the (cyclohexyl)alkylbenzene to an alkyl-biphenyl compound selected from the group consisting of one or more isomers of methylbiphenyl; 2,3-dimethylbiphenyl; 2,4-dimethylbiphenyl; 3,4-dimethylbiphenyl; and mixtures thereof;
(d) optionally, partially hydrogenating at least a portion of the alkyl-biphenyl compound, thereby obtaining an (alkylcyclohexyl)benzene selected from the group consisting of one or more isomers of (methylcyclohexyl)benzene; one or more isomers of (dimethylcyclohexyl)benzene; and mixtures thereof;
(e) optionally, transalkylating the (alkylcyclohexyl)benzene with an additional alkylbenzene selected from the group consisting of toluene, xylene, and mixtures thereof, thereby obtaining an (alkylcyclohexyl)alkylbenzene; and
(f) optionally, dehydrogenating at least a portion of the (alkylcyclohexyl)alkylbenzene to obtain a polyalkylbiphenyl compound selected from the group consisting of: one or more positional isomers of dimethylbiphenyl; one or more isomers of trimethylbiphenyl; one or more isomers of tetramethylbiphenyl; and mixtures thereof, provided that each isomer of tetramethylbiphenyl contains two methyl groups on each phenyl ring, and that each positional isomer of trimethylbiphenyl contains at least one methyl group on each phenyl ring.

21. The process of claim 20, wherein
the alkylbenzene is xylene;
the cyclohexyl-alkylbenzene is (cyclohexyl)xylene; and
the alkyl-biphenyl compound is 2,3-dimethylbiphenyl, 2,4-dimethylbiphenyl, 3,4-dimethylbiphenyl, or a mixture of any two or more of the foregoing.

22. The process of claim 21, wherein the optional steps (d), (e), and (f) are not carried out.

23. The process of claim 20, wherein
the alkylbenzene is toluene;
the cyclohexyl-alkylbenzene is (cyclohexyl)toluene; and
the alkyl-biphenyl compound methylbiphenyl;
wherein the optional steps (d), (e), and (f) are carried out, such that the (alkylcyclohexyl)benzene comprises one or more isomers of (methylcyclohexyl)benzene; the additional alkylbenzene is toluene; the (alkylcyclohexyl)alkylbenzene comprises one or more isomers of (methylcyclohexyl)toluene; and the polyalkylbiphenyl is x,y'-dimethylbiphenyl, where each of x and y is independently 2, 3, or 4.

* * * * *